United States Patent
Llop

(10) Patent No.: US 9,795,458 B2
(45) Date of Patent: Oct. 24, 2017

(54) DENTAL SURGICAL IMPLANT GUIDE AND PROSTHESIS COMBINATION AND METHOD OF USE

(71) Applicant: NATIONAL DENTEX, LLC, Palm Beach Gardens, FL (US)

(72) Inventor: Daniel R. Llop, Reno, NV (US)

(73) Assignee: NATIONAL DENTEX, LLC, Palm Beach Gardens, FL (US)

( * ) Notice: Subject to any disclaimer, the term of this patent is extended or adjusted under 35 U.S.C. 154(b) by 509 days.

(21) Appl. No.: 14/217,222

(22) Filed: Mar. 17, 2014

(65) Prior Publication Data

US 2014/0272780 A1    Sep. 18, 2014

Related U.S. Application Data

(60) Provisional application No. 61/800,987, filed on Mar. 15, 2013.

(51) Int. Cl.
| | |
|---|---|
| *A61C 3/00* | (2006.01) |
| *A61C 1/08* | (2006.01) |
| *A61C 8/00* | (2006.01) |
| *A61C 13/265* | (2006.01) |

(52) U.S. Cl.
CPC ............ *A61C 1/084* (2013.01); *A61C 8/0048* (2013.01); *A61C 13/2656* (2013.01)

(58) Field of Classification Search
CPC ... A61C 1/084; A61C 13/2656; A61C 8/0077; A61C 1/082; A61C 1/085; A61C 8/048; A61C 8/0089
See application file for complete search history.

(56) References Cited

U.S. PATENT DOCUMENTS

| | | | |
|---|---|---|---|
| 6,997,707 B2 | 2/2006 | Germanier | |
| 8,529,255 B2 | 9/2013 | Poirier et al. | |
| 2006/0223029 A1* | 10/2006 | Berger | A61C 13/275 433/172 |
| 2013/0011813 A1 | 1/2013 | Garcia et al. | |

* cited by examiner

*Primary Examiner* — Heidi M Eide
(74) *Attorney, Agent, or Firm* — Baker & McKenzie LLP

(57) ABSTRACT

The present disclosure relates, in some embodiments, to a dental prosthesis and methods of use thereof. According to some embodiments, a dental prosthesis includes a dental implant surgical guide, a prosthesis base, a prosthesis cover, at least one implant configured to be inserted through the dental implant surgical guide and the prosthesis base into a dental surgical site; and at least one implant fastener configured to attach to the at least one implant. A prosthesis base may include: a base bottom configured to sit adjacent to a dental surgical site, and a base top including a base recess, the base recess including at least one base aperture. In some embodiments, the dental implant surgical guide is configured to sit within a base recess. A prosthesis cover, in some embodiments, may include a cover recess configured to encapsulate at least a portion of the dental implant surgical guide within the base recess.

18 Claims, 3 Drawing Sheets

DENTAL SURGICAL IMPLANT GUIDE AND PROSTHESIS COMBINATION AND METHOD OF USE

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention generally relates to dental surgical implant guides. More particularity to those dental implant surgical guides that can be incorporated within a dental prosthesis's structure.

BACKGROUND

As a person ages, they generally incur expected tooth and bone loss requiring prosthesis replacement as provided by the dental profession. To remedy this loss, it is customary within the dental profession to employ several kinds of surgical guides (e.g., a bone reduction guide, an implant preparation and placement guide, etc.) for dental surgical site preparation, implant location, and the like. In addition to each of these guides having their own separate design and manufacture, the dental prosthesis has its own separate design and manufacture which may further add to the time and costs of dental prosthesis surgery. Generally, after the dental procedure is completed, these expensive guides are just discarded.

What could be needed is a dental implant surgical guide-prosthesis combination wherein the dental implant surgical guide is incorporated into the structure of a multi-piece dental prosthesis. In this manner, a base of a prosthesis incorporating the dental implant surgical guide can be placed at the dental surgical site to provide proper implant preparation and placement. Once the implants are properly secured at the dental surgical site, the prosthesis base/dental implant surgical guide can then secured to the implants. The prosthesis cover is then placed and locked upon the prosthesis base to generally encapsulate the dental implant surgical guide within the prosthesis.

SUMMARY OF ONE EMBODIMENT OF THE INVENTION

Advantages of One or More Embodiments of the Present Invention

The various embodiments of the present invention may, but do not necessarily, achieve one or more of the following advantages:

to provide an dental implant surgical guide incorporated into a dental prosthesis in a manner that reduces patient anxiety, bruising and other discomfort that may occur if the dental implant surgical guide and prosthesis were applied separately from one another;

the ability to use digital dentistry to control the design and manufacture of a dental implant surgical guide/prosthesis combination;

to provide a simplified dental implant surgical plan wherein the applications of the dental implant surgical guide and prosthesis are combined;

to provide a dental implant surgical guide/prosthesis combination that reduces cost, time and man-hours needed in a surgical procedure to properly locate and attach implants at a dental surgical site and then attach a dental prosthesis to the implants;

to provide a dental prosthesis that structurally incorporates a dental implant surgical guide that avoids the wasteful discarding of the guide after the dental surgery is completed; and the ability to increase the structural integrity of a dental prosthesis by incorporating a dental implant surgical guide into the prosthesis.

These and other advantages may be realized by reference to the remaining portions of the specification, claims, and abstract.

Brief Description of One Embodiment of the Present Invention

One possible embodiment of the invention could be a combination dental surgical implant guide and prosthesis comprising a dental implant surgical guide as supported by a prosthesis base and further enclosed by a prosthesis cover; the dental implant surgical guide is comprised of two or more double open-ended hollow master tubes connected together by one or more implant bars; the prosthesis base comprises a base body penetrated by a set of base apertures that are respectively aligned with one set of open ends of master tubes, the base body is design and manufactured to resemble a patient's gingivae; the prosthesis cover comprises a cover body penetrated by a set of cover apertures that are respectively aligned with another set of open ends of master tubes, the base body is designed and manufactured to resemble a patient's gingivae and teeth combination; wherein once implants are set at the dental surgical site using the dental implant surgical guide, implants fasteners attached to the implants secure the prosthesis base and surgical dental implant guide to the dental surgical site, the prosthesis cover then attaches to the implant fasteners to encapsulate the surgical dental implant guide.

Still another possible embodiment of the invention could be a method of using a combination dental surgical implant guide and prosthesis, comprising the following steps, providing a combination prosthesis and dental implant surgical guide comprising a dental implant surgical guide as supported by a prosthesis base and enclosed by a prosthesis cover, the dental surgical implant guide formed from master tubes being connected in series by implant bars, apertures of the prosthesis base and prosthesis cover align with open ends of the master tubes; locating the dental surgical implant guide as supported by the prosthesis base upon the surgical dental site; preparing the surgical dental site for implants using the dental surgical implant guide as supported by the prosthesis base; securing the implants to the surgical dental site using the dental surgical implant guide as supported by the prosthesis base; securing the dental surgical implant guide and prosthesis base to the implants, encapsulating dental surgical implant guide with the prosthesis cover.

The above-description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

Figure 1:
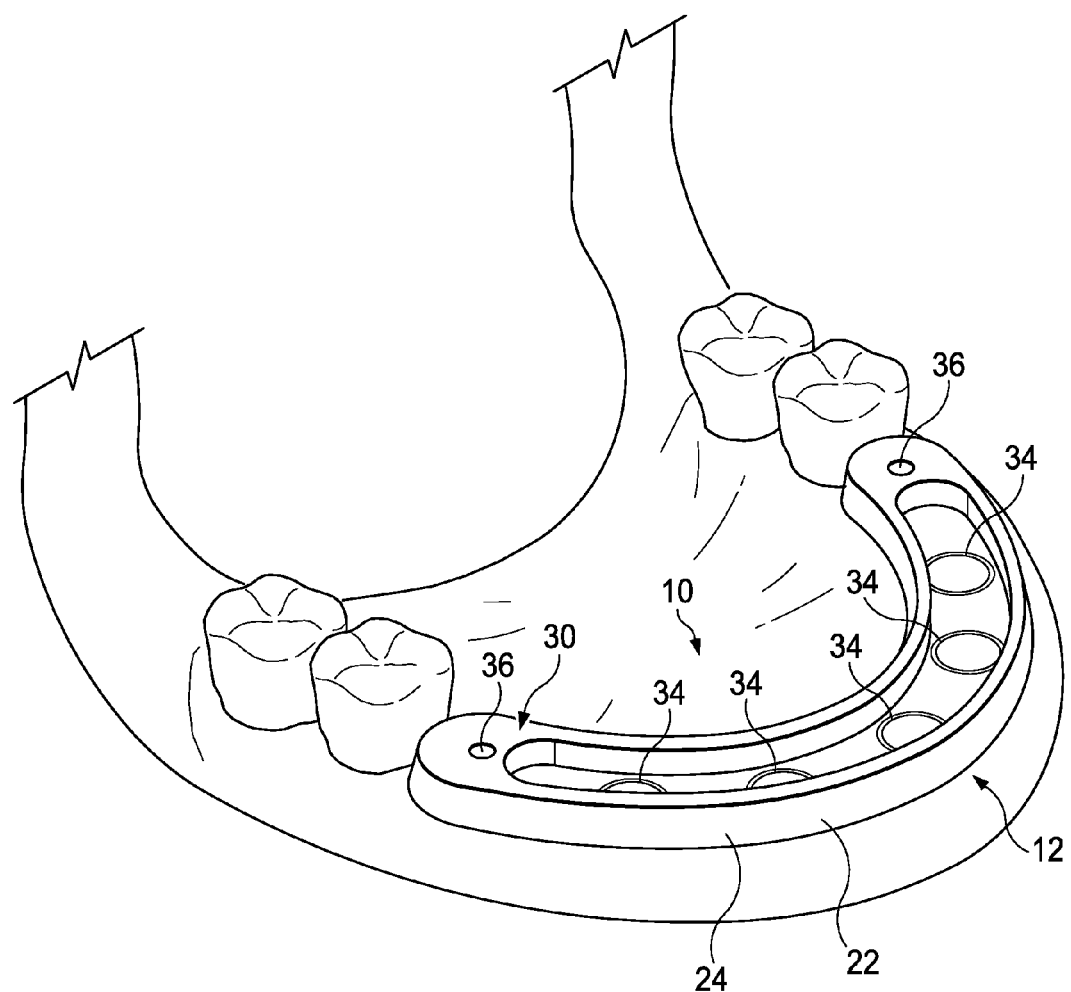
FIG. 1 is substantially a perspective view of one possible embodiment of the prosthesis base of the invention.
Figure 2:
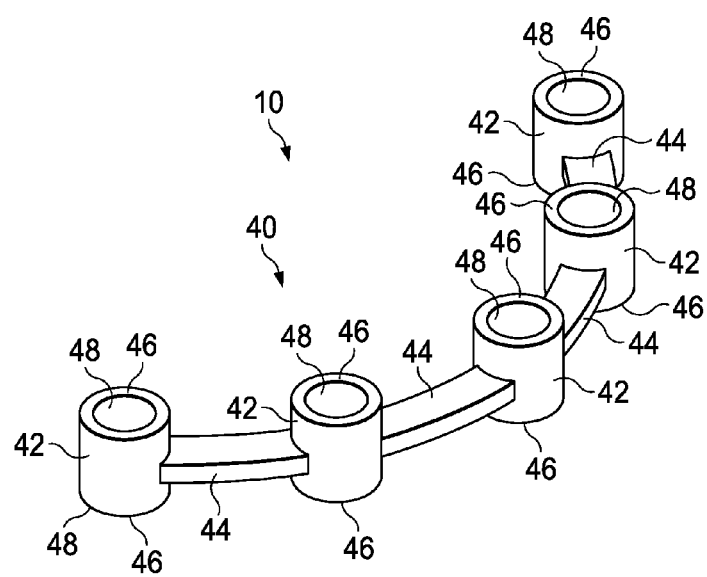
FIG. 2 is a substantially a perspective view of one possible embodiment of dental implant surgical guide of the present invention.
Figure 3:
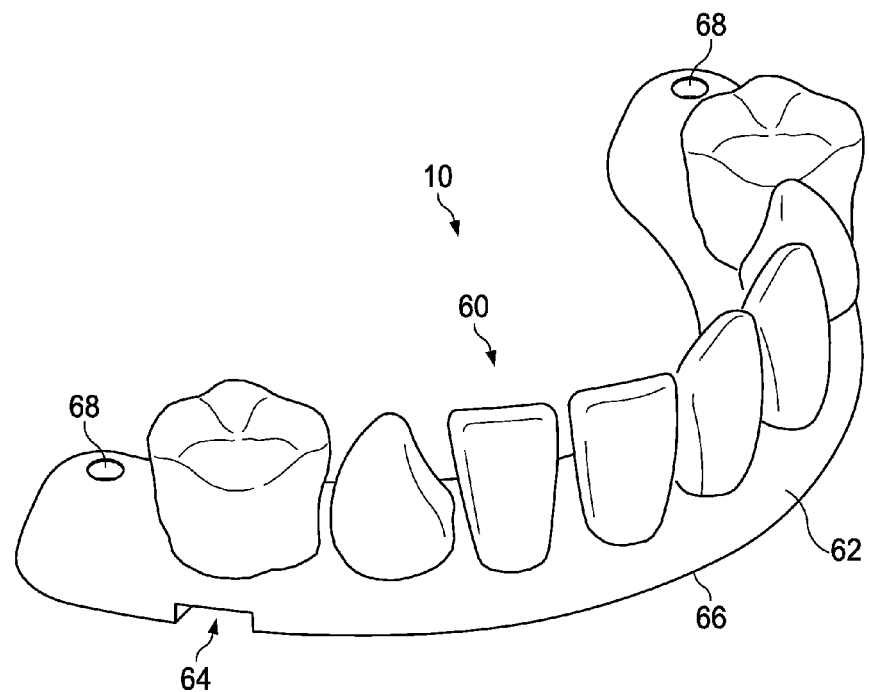
FIG. 3 is substantially a perspective view of one possible embodiment of the prosthesis cover.
Figure 4:
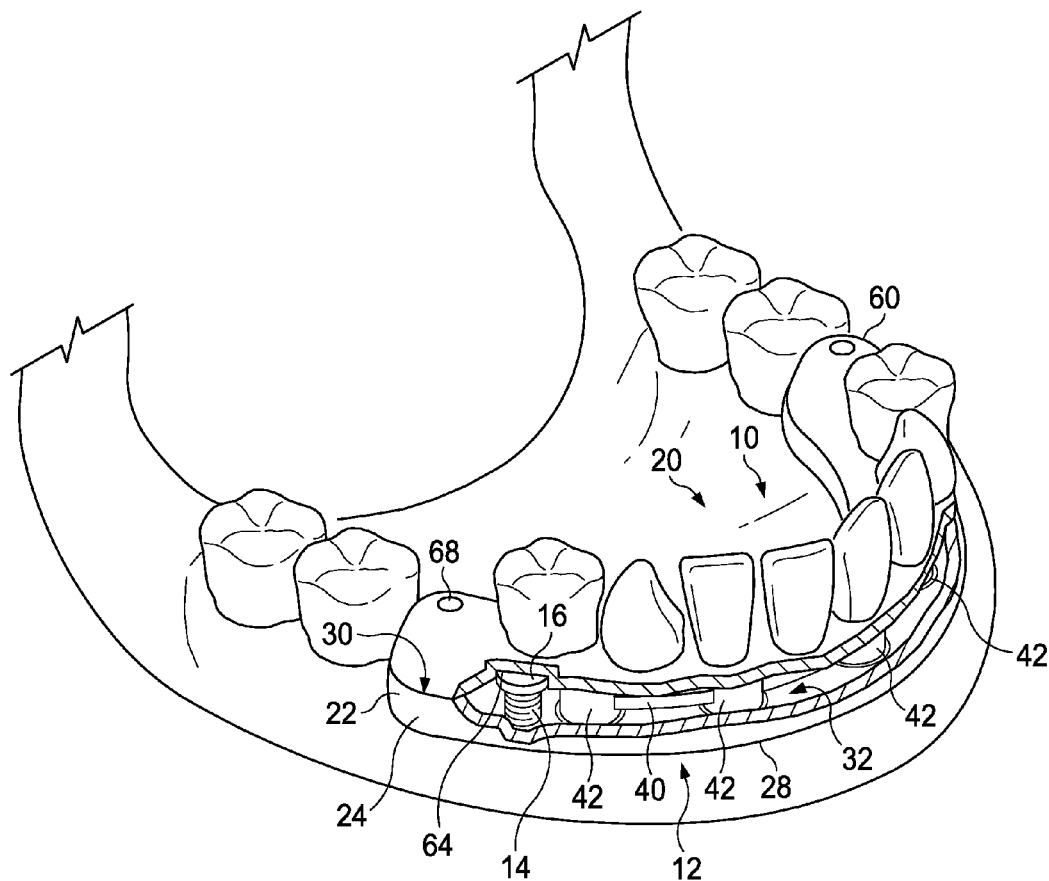
FIG. 4 is substantially a perspective cutaway view of one possible embodiment of the dental implant surgical guide/prosthesis combination.

DESCRIPTION OF CERTAIN EMBODIMENTS
OF THE PRESENT INVENTION

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

The present invention 10 could comprise of dental implant surgical guide-prosthesis combination 20 and a respective method or process of such use 100. As substantially shown in FIGS. 1 through 4, the prosthesis-dental implant surgical guide combination 20 could comprise of prosthesis base 22, a dental implant surgical guide 40 and prosthesis cover 60. The prosthesis base 22 could have a base body 24 that is made from suitable dental material normally used for such purpose and be manufactured and colored to match the patient's own gingivae that the combination 20 would supplant or otherwise cover up. Likewise, sides of the prosthesis base 22 could be constructed to have the ridges and valleys imitating that portion of the patient's mouth which the combination 20 will supplant and/or cover up. The base bottom 28 could be created to match the contour of the dental surgical site while the base top 30 could have a base recess 32 to accommodate at least a portion of the dental implant surgical guide 40 (which could be glued into place into the base recess utilizing well-known dental adhesives and the like.) The prosthesis base 22 can further have a set of base apertures 34 connecting the base top 30 to the base bottom 28 that will align with the dental implant surgically guide 40 to allow dental tools, implants and the like being guided by the dental implant surgical guide 40 to appropriately pass through the prosthesis base 22 and onto the dental surgical site 12. The prosthesis base 22 could also have one or more fastener apertures 36 which could allow suitable base fasteners (not shown) to pass through the base onto the dental surgical site 12 to reversibly secure the prosthesis base 22 to the dental surgical site 12.

The dental implant surgical guide 40 could comprise of two or more master tubes 42 connected together by one or more implant bars 44. The master tube 42 could be a double open-ended hollow cylinder wherein each open end 46 continuously connects to the hollow interior 48. The vertically-oriented master tubes 42 could be connected to another in series by implant bars 44 (e.g., in that the implant bar 44 is horizontally oriented and generally found between two master tubes 42) to generally control the overall positioning of the respective master tubes 42 relative their positions in the dental surgical site 12. Consequently, the connection of the implant bar 44 to the master tube 42 generally controls the placement, telemetry, rotation and other various directions aspects of the implant location relative to the dental surgical site 12. Generally, the surgical dental implant guide 40 further is constructed to mate with and be enclosed within the base recess 32 and cover recess 64.

The prosthesis cover 60 could have a cover body 62 that may be constructed out of suitable dental material used for that purpose to recreate gingivae and tooth replacement combination, both visually and functionally. The cover bottom 66 may be contoured to generally accommodate the base top 30 and another portion of the dental implant surgical guide 40 (e.g., within the cover recess 64.)

Once the implants 14 have been installed in the dental surgical site 12 using the invention 10, implant fasteners 16 can be attached to the tops of the respective implants 14 to operationally secure dental implant surgical guide/prosthesis base to the dental surgical site 12. The cover recess 64 and implant fasteners 16 can be mutually designed and constructed as well-known in the art so that the cover recess 64 has a snap-fit or like attachment relationship to the implant fasteners 16. The prosthesis cover 60 may further comprise the set of cover fastener apertures 68 that penetrate the prosthesis cover 60 substantially allowing suitable prosthesis fasteners (not shown) to additionally secure the prosthesis cover 60 to the prosthesis base 22.

Figure 5:
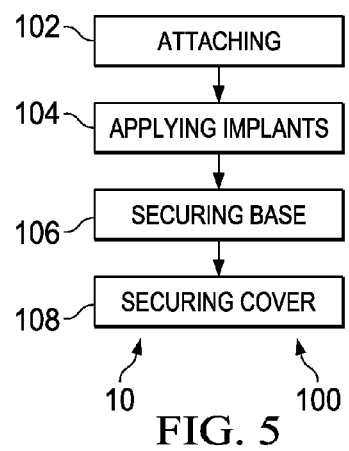
FIG. 5 is substantially a flow schematic showing a method of using the invention.

As substantially shown in FIG. 5, one possible method or process 100 for the use of the invention 10 could start with step 102, attaching the prosthesis base/dental implant surgical guide to the dental surgical site. In this step, the dental health care professional, after suitably preparing the dental surgical site as required, could place the base bottom upon the dental surgical site and use base fasteners penetrating fastener apertures to initially secure the base/dental implant surgical guide to the dental surgical site.

If the invention is further used in direct combination and lockup with a receiving bone foundation guide, the gum could be peeled back from the dental surgical site to allow the bone foundation guide to be fastened to the bared bone of dental surgical site. The bone in that area can be reduced or augmented using the bone foundation guide as required by the dental implant surgical plan. Once the bone is so treated, with the bone foundation guide still in place, a tissue spacer gasket (e.g., made of suitable elastic dental polymer material) having apertures matching the placement of master tubes and sized to meet the footprint of the base bottom, is placed upon the bone foundation guide to make up for the thickness otherwise provide by the pealed back gum tissue. With the tissue spacer gasket in place on the top of the bone foundation guide, the prosthesis/dental implant surgical guide is placed on top of the tissue spacer gasket and held in place to the bone foundation guide by suitable means.

Once step 102 is substantially completed, the process can proceed to step 104, applying the implants.

In step 104, applying the implants, with the base/dental implant surgical guide in place, the dental health care professional can use suitable implant appliances (drills, reamers, etc.) as guided by the invention 10, to properly prepare the dental surgical site to receive the implants. Once implant preparation is completed, the implants can be placed through and be guided by the prosthesis base/dental implant surgical guide to properly locate them into the dental surgical site.

If the invention 10 is used in conjunction/combination with a bone foundation guide, the invention is removed from the bone foundation guide, and the bone foundation guide (and tissue space gasket) is removed from the dental surgical site. The dental surgical site is re-sheathed with gum tissue being sutured up to enclose the otherwise open bone area less that portion now occupied by the implants. The base/dental implant surgical guide could then be placed over the implants and be otherwise re-secured to the dental surgical site (e.g., attaching implant fasteners to the top of the implants.) As step 104 is substantially completed, the process 100 could proceed to step 106 securing the prosthesis base.

In step 106, securing the prosthesis base, with the prosthesis base/dental implant surgical guide located over and to the implants, implant fasteners can be applied to the implants to secure dental implant surgical guide (and hence the prosthesis base) to the implants. Once this step is substantially completed, the process 100 could move to step 108, securing the prosthesis cover.

In step 108, securing the prosthesis cover, the prosthesis cover could be brought proximate to the exposed portion of the dental implant surgical guide so that cover recess could receive and snap/attach to the exposed portion of the implant fasteners to secure the prosthesis cover to the prosthesis base. Additionally, suitable prosthesis fasteners can be placed through cover fastener apertures to substantially allow additional attachment of the prosthesis cover to the prosthesis base. At this point, the primary dental surgery could be considered complete with invention properly attached to the patient.

CONCLUSION

Although the description above contains many specifications, these should not be construed as limiting the scope of the invention but as merely providing illustrations of some of the presently preferred embodiments of this invention. Thus, the scope of the invention should be determined by the appended claims and their legal equivalents rather than by the examples given.

As seen through the specifications and drawings, the invention can be considered a dental appliance combination that incorporates a dental implant surgical guide into a dental prosthesis that increases the structural integrity of the prosthesis and avoids wasteful discardment of the guide after the completion of the dental implant surgery. In combining these dental implements together, the time, cost, man-hours, patient discomfort and anxiety can be significantly reduced for such dental implant surgeries.

What is claimed is:

1. A dental prosthesis comprising:
   a dental implant surgical guide comprising:
      a first master tube comprising a first hollow cylinder extending continuously in a vertical direction from a first open end to a second open end,
      a second master tube comprising a second hollow cylinder extending continuously in the vertical direction from a third open end to a fourth open end, and
      an implant bar horizontally connecting the first hollow cylinder to the second hollow cylinder;
   a prosthesis base comprising:
      a base bottom configured to sit adjacent to a dental surgical site, and
      a base top comprising a base recess, the base recess comprising at least one base aperture configured to (a) penetrate at least a portion of the base bottom and the base recess and (b) align with at least one of the first master tube and the second master tube and permitting a dental tool to access the dental surgical site through the first hollow cylinder of the first master tube or the second hollow cylinder of the second master tube;
   a prosthesis cover comprising a cover recess configured to encapsulate at least a portion of the dental implant surgical guide within the base recess;
   at least one implant configured to be inserted through the dental implant surgical guide and the prosthesis base into the dental surgical site; and
   at least one implant fastener configured to attach to the at least one implant.

2. The dental prosthesis of claim 1 wherein the prosthesis cover further comprises at least one cover fastener aperture and at least one prosthesis fastener,
   wherein the at least one cover fastener aperture is configured to penetrate the prosthesis cover, and
   wherein the at least one prosthesis fastener is configured to secure at least a portion of the prosthesis cover to at least a portion of the prosthesis base.

3. The dental prosthesis of claim 1, wherein the dental implant surgical guide is configured to mate with the base recess.

4. The dental prosthesis of claim 1, wherein the cover recess is configured to receive a portion of the at least one implant fastener in a snap-fit relationship.

5. The dental prosthesis of claim 1, wherein the prosthesis cover is configured to receive a portion of the at least one implant fastener in a snap-fit relationship.

6. The dental prosthesis of claim 1, wherein the dental implant surgical guide further comprises:
   a third master tube comprising a third hollow cylinder extending continuously in the vertical direction from a fifth open end to a sixth open end, and
   a second implant bar horizontally connecting the second hollow cylinder to the third hollow cylinder.

7. The dental prosthesis of claim 6, wherein the dental implant surgical guide further comprises:
   a fourth master tube comprising a fourth hollow cylinder extending continuously in the vertical direction from a seventh open end to an eighth open end, and
   a third implant bar horizontally connecting the third hollow cylinder to the fourth hollow cylinder.

8. The dental prosthesis of claim 1, wherein the cover recess is configured to encapsulate the entire dental implant surgical guide within the base recess.

9. The dental prosthesis of claim 1, the prosthesis base further comprising:
   at least one base fastener configured to attach the prosthesis base to the dental surgical site, and
   at least one fastener aperture configured to penetrate at least a portion of the prosthesis base, align with at least a portion of the dental surgical site, and receive the at least one base fastener.

10. The dental prosthesis of claim 1, wherein the prosthesis base is configured to correspond a shaping of at least a portion of a patient's gingivae, or a coloration of at least a portion of the patient's gingivae, or both.

11. The dental prosthesis of claim 1, wherein the prosthesis cover is further configured to resemble gingivae and at least one tooth.

12. A method of using a dental prosthesis, the method comprising:
providing a dental implant surgical guide, the dental implant surgical guide comprising:
a first master tube comprising a first hollow cylinder extending continuously in a vertical direction from a first open end to a second open end,
a second master tube comprising a second hollow cylinder extending continuously in the vertical direction from a third open end to a fourth open end, and
an implant bar horizontally connecting the first hollow cylinder to the second hollow cylinder;
providing a prosthesis base, the prosthesis base comprising:
a base bottom configured to sit adjacent to a dental surgical site, and
a base top comprising a base recess, the base recess comprising at least one base aperture configured to (a) penetrate at least a portion of the base bottom and the base recess and (b) align with at least one of the first master tube and the second master tube and permitting a dental tool to access the dental surgical site through the first hollow cylinder of the first master tube or the second hollow cylinder of the second master tube,
placing the base bottom adjacent to the dental surgical site;
aligning at least one of the first master tube and the second master tube with the at least one base aperture of the base recess;
inserting the dental tool through at least one of the first hollow cylinder of the first master tube or the second hollow cylinder of the second master tube to generate an implant passage;
inserting an implant into the implant passage;
providing a prosthesis cover comprising:
a cover bottom configured to align with at least a portion of the base top, and
a cover recess configured to encapsulate the dental implant surgical guide within the base recess;
placing the cover bottom adjacent to at least a portion of the base top to encapsulate at least a portion of the dental implant surgical guide.

13. The method of claim 12 further comprising fitting an implant fastener on the implant.

14. The method of claim 12 further comprises securing at least a portion of the prosthesis cover to at least a portion of the prosthesis base by receiving at least one prosthesis cover fastener into at least one prosthesis cover aperture.

15. The dental prosthesis of claim 13,
wherein providing the prosthesis cover further comprises configuring the cover recess to receive a portion of the implant fastener in a snap-fit relationship, and
wherein the method further comprises the cover recess receiving the portion of the implant fastener in the snap-fit relationship.

16. The method of claim 12, further comprising attaching the prosthesis base to the dental surgical site,
wherein the prosthesis base further comprises:
at least one base fastener configured to attach the prosthesis base to the dental surgical site, and
at least one fastener aperture configured to penetrate at least a portion of the prosthesis base, align with at least a portion of the dental surgical site, and receive the at least one base fastener, and
wherein attaching the prosthesis base to the dental surgical site comprises securing the at least one base fastener through the at least one fastener aperture.

17. The method of claim 12 further comprising securing at least a portion of the dental implant surgical guide to the base recess using a dental adhesive.

18. The method of claim 12 wherein providing the prosthesis base further comprises designing the base bottom to have at least one of: a contour that corresponds to the dental surgical site and is configured to sit adjacent to the dental surgical site; a shaping that corresponds to at least a portion of a patient's gingivae; and a coloration that corresponds to at least a portion of the patient's gingivae.

* * * * *